United States Patent
Lyth

(10) Patent No.: US 7,390,355 B2
(45) Date of Patent: Jun. 24, 2008

(54) ZINC OXIDE

(75) Inventor: Philip Laurence Lyth, Stockton-on-Tees (GB)

(73) Assignee: Croda International Plc, Goole, East Yorkshire (GB)

( * ) Notice: Subject to any disclaimer, the term of this patent is extended or adjusted under 35 U.S.C. 154(b) by 55 days.

(21) Appl. No.: 10/559,276

(22) PCT Filed: Jun. 10, 2004

(86) PCT No.: PCT/GB2004/002480

§ 371 (c)(1),
(2), (4) Date: Dec. 2, 2005

(87) PCT Pub. No.: WO2004/108599

PCT Pub. Date: Dec. 16, 2004

(65) Prior Publication Data

US 2006/0228310 A1    Oct. 12, 2006

(30) Foreign Application Priority Data

Jun. 11, 2003 (GB) ................................ 0313432.7

(51) Int. Cl.
*C04B 14/00* (2006.01)

(52) U.S. Cl. .................. 106/401; 106/419; 106/425; 106/429; 106/432; 106/442; 106/443; 106/447; 106/450; 106/471; 252/500; 424/59; 428/403; 428/447; 516/33

(58) Field of Classification Search ............... 252/500; 242/59; 106/401, 419, 425, 429, 432, 442, 106/443, 447, 450, 455, 460, 471; 516/33; 428/447, 403; 524/588; 424/59

See application file for complete search history.

(56) References Cited

U.S. PATENT DOCUMENTS

| | | | | | |
|---|---|---|---|---|---|
| 5,366,660 | A | * | 11/1994 | Tapley | 516/33 |
| 5,573,753 | A | * | 11/1996 | Tapley | 424/59 |
| 5,575,988 | A | * | 11/1996 | Knowles et al. | 424/59 |
| 5,605,652 | A | * | 2/1997 | Tapley | 424/59 |
| 5,914,101 | A | * | 6/1999 | Tapley et al. | 424/59 |
| 6,683,130 | B2 | * | 1/2004 | Kessell | 524/588 |
| 7,101,427 | B2 | * | 9/2006 | Dransfield et al. | 106/401 |
| 2002/0054999 | A1 | * | 5/2002 | Kessell | 428/447 |
| 2003/0161795 | A1 | * | 8/2003 | Tsuzuki et al. | 424/59 |
| 2005/0069706 | A1 | * | 3/2005 | Kessell | 428/403 |

FOREIGN PATENT DOCUMENTS

| | | | |
|---|---|---|---|
| EP | 0535971 | | 4/1993 |
| EP | 0535972 | | 4/1993 |
| JP | 02-289506 | * | 8/1989 |
| JP | 11-106216 | * | 10/1997 |

OTHER PUBLICATIONS

Abstract of Guo-Dong Li et al., "Study on preparation of low cost, non-aggregation ZnO nanoparticles".

* cited by examiner

*Primary Examiner*—Mark Kopec
*Assistant Examiner*—Khanh T Nguyen
(74) *Attorney, Agent, or Firm*—Jones Day

(57) ABSTRACT

A dispersion containing zinc oxide particles having a dispersion particle size of (i) median volume particle diameter in the range from 70 to 130 nm, (ii) less than 16% by volume of particles having a volume diameter of less than 35 nm below the median volume particle diameter, and (iii) more than 84% by volume of particles having a volume diameter of less than 57 nm above the median volume particle diameter. The zinc oxide dispersion can be used in a sunscreen product that exhibits both effective UV protection and improved transparency. The zinc oxide is particularly suitable for use in combination with transparent titanium dioxide.

22 Claims, No Drawings

ZINC OXIDE

CROSS REFERENCE TO RELATED APPLICATION

This application is the National Phase application of International Application No. PCT/GB2004/002480, filed Jun. 10, 2004, which designates the United States and was published in English. This application, in its entirety, is incorporated herein by reference.

FIELD OF INVENTION

The present invention relates to zinc oxide, in particular in the form of a dispersion, and to the use thereof in a sunscreen product.

BACKGROUND

Zinc oxide has been employed as an attenuator of ultraviolet light in cosmetic and sunscreen applications. Due to the increased awareness of the link between ultraviolet light and skin cancer, there has been an increasing requirement for ultraviolet light protection in everyday skincare and cosmetics products. Unfortunately, existing commercially available zinc oxide products are not sufficiently transparent and can have an unacceptable whitening effect when used on the skin. There is a need for a zinc oxide in a form, particularly when used in combination with titanium dioxide, which exhibits improved transparency, reduced whitening, and provides broad spectrum ultraviolet light protection.

REVIEW OF THE PRIOR ART

EP-0535971-B is directed to an oil dispersion of zinc oxide particles.

SUMMARY OF THE INVENTION

We have now surprisingly discovered an improved zinc oxide, which overcomes or significantly reduces at least one of the aforementioned problems.

Accordingly, the present invention provides a dispersion comprising particles of zinc oxide in a dispersing medium wherein the zinc oxide particles in dispersion have (i) a median volume particle diameter in the range from 70 to 130 nm, (ii) less than 16% by volume of particles having a volume diameter of less than 35 nm below the median volume particle diameter, and (iii) more than 84% by volume of particles having a volume diameter of less than 57 nm above the median volume particle diameter.

The invention also provides a particulate zinc oxide having a dispersion particle size of (i) median volume particle diameter in the range from 70 to 130 nm, (ii) less than 16% by volume of particles having a volume diameter of less than 35 nm below the median volume particle diameter, and (iii) more than 84% by volume of particles having a volume diameter of less than 57 nm above the median volume particle diameter.

The invention further provides a particulate zinc oxide having an extinction coefficient at 524 nm ($E_{524}$) in the range from 0.1 to 1.0 l/g/cm an extinction coefficient at 450 nm ($E_{450}$) in the range from 0.3 to 2 l/g/cm an extinction coefficient at 360 nm ($E_{360}$) in the range from 11 to 20 l/g/cm an extinction coefficient at 308 nm ($E_{308}$) in the range from 11 to 20 l/g/cm a maximum extinction coefficient E(max) in the range from 12 to 20 l/g/cm, and a λ(max) in the range from 363 to 377 nm.

The invention further provides a sunscreen product comprising a zinc oxide or dispersion as defined herein.

The invention further provides the use of a zinc oxide or dispersion as defined herein in the manufacture of a sunscreen having reduced whiteness.

The invention still further provides a sunscreen product comprising (a) zinc oxide having a dispersion particle size of (i) median volume particle diameter in the range from 70 to 130 nm, (ii) less than 16% by volume of particles having a volume diameter of less than 35 nm below the median volume particle diameter, and (iii) more than 84% by volume of particles having a volume diameter of less than 57 nm above the median volume particle diameter, and (b) titanium dioxide having a dispersion particle size of (i) median volume particle diameter in the range from 24 to 42 nm, (ii) less than 16% by volume of particles having a volume diameter of less than 15 nm below the median volume particle diameter, and (iii) more than 84% by volume of particles having a volume diameter of less than 20 nm above the median volume particle diameter.

The particulate zinc oxide used in the present invention comprises primary particles suitably having a mean particle size (measured as described herein) in the range from 35 to 65 nm, preferably 40 to 60 nm, more preferably 45 to 55 nm, particularly 48 to 52 nm, and especially 49 to 51 nm. The size distribution of the primary zinc oxide particles can have a significant effect on the final properties of, for example, a sunscreen product comprising the zinc oxide. In a preferred embodiment of the invention suitably at least 50%, preferably at least 60%, more preferably at least 70%, particularly at least 80%, and especially at least 90% by number of particles have a particle size within the above preferred ranges given for the mean particle size.

The primary zinc oxide particles are preferably approximately spherical, preferably having a mean aspect ratio $d_1:d_2$ (where $d_1$ and $d_2$, respectively, are the length and width of the particle (measured as described herein)) in the range from 0.6 to 1.4:1, more preferably 0.7 to 1.3:1, particularly 0.8 to 1.2:1, and especially 0.9 to 1.1:1. In a preferred embodiment of the invention, suitably at least 40%, preferably at least 55%, more preferably at least 70%, particularly at least 80%, and especially at least 90% by number of particles have an aspect ratio within the above preferred ranges given for the mean aspect ratio.

When formed into a dispersion according to the present invention, the particulate zinc oxide suitably has a median volume particle diameter (equivalent spherical diameter corresponding to 50% of the volume of all the particles, read on the cumulative distribution curve relating volume % to the diameter of the particles—often referred to as the "D(v,0.5)" value)) (hereinafter referred to as dispersion particle size), measured as herein described, in the range from 70 to 130 nm, suitably 80 to 120 nm, preferably 87 to 113, more preferably 93 to 107 nm, particularly 97 to 103 nm, and especially 99 to 101 nm.

The size distribution of the zinc oxide particles in dispersion can also be an important parameter in obtaining, for example, a sunscreen product having the required properties. The zinc oxide particles suitably have less than 16% by volume of particles having a volume diameter of less than 35 nm, preferably less than 33 nm, more preferably less than 30 nm, particularly less than 25 nm, and especially less than 20 nm below the median volume particle diameter. In addition, the zinc oxide particles suitably have less than 30% by volume of particles having a volume diameter of less than 19 nm, preferably less than 18 nm, more preferably less than 16 nm, particularly less than 12 nm, and especially less than 8 nm below the median volume particle diameter.

Further, the zinc oxide particles in dispersion suitably have more than 84% by volume of particles having a volume diameter of less than 57 nm, preferably less than 54 nm, more preferably less than 50 nm, particularly less than 45 nm, and especially less than 40 nm above the median volume particle diameter. Also, the zinc oxide particles suitably have more than 70% by volume of particles having a volume diameter of less than 24 nm, preferably less than 23 nm, more preferably less than 21 nm, particularly less than 16 nm, and especially less than 10 nm above the median volume particle diameter.

It is preferred that none of the zinc oxide particles in dispersion should have an actual particle size exceeding 200 nm. Particles exceeding such a size may be removed by milling processes which are known in the art. However, milling operations are not always totally successful in eliminating all particles greater than a chosen size. In practice, therefore, the size of 95%, preferably 99% by volume of the particles should not exceed 200 nm, preferably 150 nm.

Particle size of the zinc oxide particles in dispersion may be measured by electron microscope, coulter counter, sedimentation analysis and static or dynamic light scattering. Techniques based on sedimentation analysis are preferred. The median particle size may be determined by plotting a cumulative distribution curve representing the percentage of particle volume below chosen particle sizes and measuring the 50th percentile. The median particle volume diameter of the zinc oxide particles in dispersion is suitably measured using a Brookhaven particle sizer, as described herein. The particle size distributions can also be obtained from the same cumulative distribution curve.

In a particularly preferred embodiment of the invention, the zinc oxide particles suitably have a BET specific surface area (measured as described herein) in the range from 10 to 40, preferably 15 to 35, more preferably 20 to 30, particularly 23 to 27, and especially 24 to 26 $m^2/g$.

The particulate zinc oxide used in the present invention may be formed by any suitable process and typical processes are the French Method in which metallic zinc is melted and evaporated before being oxidized in the gas phase, the American method in which zinc ores are sintered and reduced with cokes and the zinc thus obtained is oxidised to zinc oxide, and a wet method in which a water soluble zinc salt such as zinc chloride or zinc sulphate is crystallised and then converted to zinc oxide by sintering. Fractionation techniques, as known in the art, e.g. micronisation, sedimentation, or centrifugation, may be employed in order to obtain zinc oxide having the required particle size and size distribution as defined herein.

The particles of zinc oxide may comprise substantially pure zinc oxide, but in one embodiment of the invention the particles have an inorganic and/or organic coating. The inorganic coating is preferably one or more oxides or hydrous oxides, for example aluminium, silicon, titanium, zirconium, magnesium or zinc. The organic coating may be a fatty acid, an organic silicon compound, polyol, amine and/or alkanolamine. The coating is usually chosen to ensure compatibility with the particular medium that will be used with the zinc oxide particles. Thus, inorganic hydrophilic coatings are normally preferred for incorporating the zinc oxide particles in aqueous media, and organic hydrophobic coatings for organic, particularly oil, media.

The level of purity of the zinc oxide particles is an important requirement for use, for example, in cosmetic and sunscreen applications. In a preferred embodiment, the lead content of the zinc oxide particles (uncoated and/or coated) is preferably less than 15 ppm, more preferably less than 13 ppm, particularly less than 10 ppm, and especially less than 6 ppm.

The zinc oxide particles used in the present invention exhibit improved transparency suitably having an extinction coefficient at 524 nm ($E_{524}$) (measured as described herein) of less than 1.5, preferably less than 1.2, more preferably in the range from 0.1 to 1.0, particularly 0.3 to 0.9, and especially 0.5 to 0.8 l/g/cm. In addition, the zinc oxide particles suitably have an extinction coefficient at 450 nm ($E_{450}$) (measured as described herein) of less than 3, preferably less than 2.5, more preferably in the range from 0.3 to 2, particularly 0.6 to 1.7, and especially 1 to 1.5 l/g/cm.

The zinc oxide particles exhibit effective UV absorption, suitably having an extinction coefficient at 360 nm ($E_{360}$) (measured as described herein) of greater than 10, preferably in the range from 11 to 20, more preferably 12 to 17, particularly 13 to 15, and especially 13.5 to 14.5 l/g/cm. The zinc oxide particles also suitably have an extinction coefficient at 308 nm ($E_{308}$) (measured as described herein) of greater than 10, preferably in the range from 11 to 20, more preferably 11.5 to 16, particularly 12 to 14, and especially 12.5 to 13.5 l/g/cm.

The zinc oxide particles suitably have a maximum extinction coefficient E(max) (measured as described herein) in the range from 10 to 25, preferably 12 to 20, more preferably 13 to 18, particularly 14 to 17, and especially 15 to 16 l/g/cm. The zinc oxide particles suitably have a λ(max) (measured as described herein) in the range from 360 to 380, preferably 363 to 377, more preferably 366 to 375, particularly 368 to 373, and especially 369 to 372 nm.

The zinc oxide particles can exhibit reduced whiteness, suitably having a change in whiteness ΔL of a sunscreen product containing the particles (measured as described herein) of less than 3.5, preferably less than 3, more preferably less than 2.5, particularly less than 2.0, and especially less than 1.5. In addition, a sunscreen product containing the zinc oxide particles suitably has a whiteness index (measured as described herein) of less than 90%, preferably in the range from 5 to 80%, more preferably 10 to 70%, particularly 15 to 60%, and especially 20 to 50%.

A composition, preferably a sunscreen product, containing the zinc oxide particles defined herein as substantially the sole sunscreen agent, suitably has a Sun Protection Factor (SPF) (measured as described herein) of greater than 4, preferably greater than 6, more preferably greater than 9, particularly in the range from 12 to 20, and especially 15 to 18.

The particulate zinc oxide may be formed into a dispersion, in any suitable aqueous of organic liquid medium. By dispersion is meant a true dispersion, i.e. where the solid particles are stable to aggregation. The particles in the dispersion are relatively uniformly dispersed and resistant to settling out on standing, but if some settling out does occur, the particles can be easily redispersed by simple agitation.

Cosmetically acceptable materials are preferred as the liquid medium. A useful organic medium is a liquid oil such as vegetable oils, e.g. fatty acid glycerides, fatty acid esters and fatty alcohols. A preferred organic medium is a siloxane fluid, especially a cyclic oligomeric dialkylsiloxane, such as the cyclic pentamer of dimethylsiloxane known as cyclomethicone. Alternative fluids include dimethylsiloxane linear oligomers or polymers having a suitable fluidity and phenyltris (trimethylsiloxy)silane (also known as phenyltrimethicone).

Examples of suitable organic media include avocado oil, C12-15 alkyl benzoate, C12-15 alkyl ethylhexanoate, C12-15 alkyl lactate, C12-15 alkyl salicylate, C13-14 isoparaffin, C18-36 acid glycol ester, C18-36 acid triglyceride, caprylic/capric glycerides, caprylic/capric triglyceride, caprylic/capric/lauric triglyceride, caprylic/capric/linoleic triglyceride, caprylic/capric/myristic/stearic triglyceride, caprylic/capric/ stearic triglyceride, castor oil, castor oil-silicone ester, cetearyl ethylhexanoate, cetearyl isononanoate, cetearyl palmitate, cetearyl stearate, cetyl dimethicone, cetyl dimethicone copolyol, cetyl ethylhexanoate, cetyl glycol isostearate, cetyl isononanoate, cetyl lactate, cetyl myristate, cetyl oleate, cetyl palmitate, cetyl ricinoleate, cetyl stearate, cocoglycerides, coconut oil, cyclomethicone, cyclopentasiloxane, cyclotetrasiloxane, decyl isostearate, decyl oleate, decyl polyglucoside, dibutyl adipate, diethylhexyl dimer dilinoleate, diethylhexyl malate, diisopropyl adipate, diisopropyl dimer dilinoleate, diisostearyl adipate, diisostearyl dimer dilinoleate, diisostearyl malate, diisostearyl trimethylolpropane siloxy silicate, dilauryl trimethylolpropane siloxy silicate, dimethicone, dimethicone copolyol, dimethicone propyl PG-betaine, dimethiconol, dimethyl isosorbide, dioctyl maleate, dioctylodedecyl dimer dilonoleate, ethylhexyl benzoate, ethylhexyl cocoate, ethylhexyl dimethyl PABA, ethylhexyl ethylhexanoate, ethylhexyl hydroxystearate, ethylhexyl hydroxystearate benzoate, ethylhexyl isononanoate, ethylhexyl isopalmitate, ethylhexyl isostearate, ethylhexyl laurate, ethylhexyl methoxycinnamate, ethylhexyl myristate, ethylhexyl neopentanoate, ethylhexyl oleate, ethylhexyl palmitate, ethylhexyl salicylate, ethylhexyl stearate, glyceryl caprate, glyceryl caprylate, glyceryl caprylate/caprate, glyceryl cocoate, glyceryl dilaurate, glyceryl dioleate, glyceryl hydroxystearate, glyceryl isostearate, glyceryl laurate, glyceryl oleate, glycol oleate, glycol ricinoleate, helianthus annuus (hybrid sunflower) seed oil, helianthus annuus (sunflower) seed oil, homosalate, isoamyl laurate, isoamyl p-methoxycinnamate, isocetyl alcohol, isocetyl behenate, isocetyl ethylhexanoate, isocetyl isostearate, isocetyl laurate, isocetyl linoleoyl stearate, isocetyl myristate, isocetyl palmitate, isocetyl salicylate, isocetyl stearate, isocetyl stearoyl stearate, isohexadecane, isononyl isononanoate, isopropyl C12-15-pareth-9 carboxylate, isopropyl isostearate, isopropyl lanolate, isopropyl laurate, isopropyl linoleate, isopropyl methoxycinnamate, isopropyl myristate, isopropyl oleate, isopropyl palmitate, isopropyl PPG-2-isodeceth-7 carboxylate, isopropyl ricinoleate, isopropyl stearate, isostearic acid, isostearyl alcohol, isostearyl ethylhexanoate, isostearyl isononanoate, isostearyl isostearate, isostearyl lactate, isostearyl myristate, isostearyl neopentanoate, isostearyl palmitate, isostearyl stearoyl stearate, jojoba oil, lanolin (lanolin oil), maleated soybean oil, myristyl isostearate, myristyl lactate, myristyl myristate, myristyl neopentanoate, myristyl stearate, octocrylene, octyldecanol, octyidodecanol, oenothera biennis (evening primrose oil), paraffinum liquidum (mineral oil), PCA dimethicone, pentaerythrityl tetraisononanoate, pentaerythrityl tetraisostearate, perfluoropolymethylisopropyl ether, persea gratissima (avocado oil), phenyl trimethicone, PPG-15 stearyl ether, propylene glycol ceteth-3 acetate, propylene glycol dicaprylate, propylene glycol dicaprylate/dicaprate, propylene glycol dipelargonate, propylene glycol distearate, propylene glycol isoceteth-3 acetate, propylene glycol isostearate, propylene glycol laurate, proylene glycol ricinoleate, propylene glycol stearate, prunus dulcis (sweet almond oil), squalane, squalene, tricaprylin, tricaprylyl citrate, tridecyl ethylhexanoate, tridecyl neopentanoate, tridecyl stearoyl stearate, triethylhexanoin, triethylhexyl citrate, trihydroxystearin, triisocetyl citrate, triisostearin, triisostearyl citrate, trimethylolpropane triisostearate, trimethylsiloxysilicate, triticum vulgare (wheat germ oil), vitis vinifera (grape) seed oil, and mixtures thereof.

The zinc oxide dispersions may also contain a dispersing agent in order to improve the properties thereof. The dispersing agent is preferably present in the range from 1 to 50%, more preferably 3 to 30%, particularly 5 to 20%, and especially 8 to 15% by weight based on the total weight of zinc oxide particles.

Suitable dispersing agents for use in an organic medium include substituted carboxylic acids, soap bases and polyhydroxy acids. Typically the dispersing agent can be one having a formula X.CO.AR in which A is a divalent bridging group, R is a primary secondary or tertiary amino group or a salt thereof with an acid or a quaternary ammonium salt group and X is the residue of a polyester chain which together with the —CO— group is derived from a hydroxy carboxylic acid of the formula HO—R'—COOH. As examples of typical dispersing agents are those based on ricinoleic acid, hydroxystearic acid, hydrogenated castor oil fatty acid which contains in addition to 12-hydroxystearic acid small amounts of stearic acid and palmitic acid. Dispersing agents based on one or more polyesters or salts of a hydroxycarboxylic acid and a carboxylic acid free of hydroxy groups can also be used. Compounds of various molecular weights can be used. Other suitable dispersing agents are those monoesters of fatty acid alkanolamides and carboxylic acids and their salts. Alkanolamides are based on ethanolamine, propanolamine or aminoethyl ethanolamine for example. Alternative dispersing agents are those based on polymers or copolymers of acrylic or methacrylic acids, e.g. block copolymers of such monomers. Other dispersing agents of similar general form are those having epoxy groups in the constituent radicals such as those based on the ethoxylated phosphate esters. The dispersing agent can be one of those commercially referred to as a hyper dispersant.

Suitable dispersing agents for use in an aqueous medium include a polymeric acrylic acid or a salt thereof. Partially or fully neutralized salts are usable e.g. the alkali metal salts and ammonium salts. Examples of dispersing agents are polyacrylic acids, substituted acrylic acid polymers, acrylic copolymers, sodium and/or ammonium salts of polyacrylic acids and sodium and/or ammonium salts of acrylic copolymers. Such dispersing agents are typified by polyacrylic acid itself and sodium or ammonium salts thereof as well as copolymers of an acrylic acid with other suitable monomers such as a sulphonic acid derivative such as 2-acrylamido 2-methyl propane sulphonic acid. Comonomers polymerisable with the acrylic or a substituted acrylic acid can also be one containing a carboxyl grouping. Usually the dispersing agents have a molecular weight of from 1,000 to 10,000 and are substantially linear molecules.

One feature of the present invention is that liquid dispersions, particularly in an organic medium, can be produced which contain at least 30%, suitably at least 40%, preferably at least 50%, more preferably at least 55%; particularly at least 60%, especially at least 65%, and generally up to 75% by weight of the total weight of the dispersion, of zinc oxide particles.

Alternatively, the particulate zinc oxide may be in the form of a lotion or cream of a solid and/or semi-solid dispersion. Suitable solid or semi-solid dispersions may contain, for example, in the range from 50 to 90%, preferably 60 to 85% by weight of particulate zinc oxide according to the present invention, together with any one or more of the liquid media disclosed herein, or a high molecular polymeric material, such as a wax.

The dispersions of the present invention are useful as ingredients for preparing sunscreen compositions, especially in the form of emulsions. The dispersion may further contain conventional additives suitable for use in the intended application, such as conventional cosmetic ingredients used in sunscreens.

The particulate zinc oxide described herein may provide the only ultraviolet light attenuators in a sunscreen product according to the invention, but other sunscreening agents, such as other metal oxides and/or other organic materials may also be added. For example, the zinc oxide particles described herein may be used in combination with existing commercially available zinc oxide and/or titanium dioxide sunscreens. Suitable organic sunscreens for use with zinc oxide according to the invention include p-methoxy cinnamic acid esters, salicylic acid esters, p-amino benzoic acid esters, non-sulphonated benzophenone derivatives, derivatives of dibenzoyl methane and esters of 2-cyanoacrylic acid. Specific examples of useful organic sunscreens include benzophenone-1, benzophenone-2, benzophenone-3, benzophenone-6, benzophenone-8, benzophenone-12, isopropyl dibenzoyl methane, butyl methoxy dibenzoyl methane, ethyl dihydroxypropyl PABA, glyceryl PABA, ethylhexyl dimethyl PABA, ethylhexyl methoxycinnamate, homosalate, ethylhexyl salicylate, ethylhexyl triazone, octocrylene, etocrylene, menthyl anthranilate, 4-methylbenzylidene camphor, benzophenone 4, and phenyl benzimidazole sulphonic acid.

In a particular preferred embodiment of the present invention, the particulate zinc oxide described herein is used in combination with transparent particulate titanium dioxide.

The individual or primary transparent titanium dioxide particles, used in combination with the zinc oxide particles described herein, are preferably acicular in shape and have a long axis (maximum dimension or length) and short axis (minimum dimension or width). The third axis of the particles (or depth) is preferably approximately the same dimensions as the width. The mean length by number of the primary titanium dioxide particles is suitably in the range from 50 to 90 nm, preferably 55 to 85 nm, more preferably 60 to 80 nm, particularly 65 to 77 nm, and especially 69 to 73 nm. The mean width by number of the particles is suitably in the range from 5 to 20 nm, preferably 8 to 19 nm, more preferably 10 to 18 nm, particularly 12 to 17 nm, and especially 14 to 16 nm. The primary titanium dioxide particles preferably have a mean aspect ratio $d_1:d_2$ (where $d_1$ and $d_2$, respectively, are the length and width of the particle) in the range from 2.0 to 8.0:1, more preferably 3.0 to 6.5:1, particularly 4.0 to 6.0:1, and especially 4.5 to 5.5:1.

The transparent titanium dioxide suitably has a dispersion particle size of (i) median volume particle diameter in the range from 24 to 42 nm, preferably 27 to 39 nm, more preferably 29 to 37 nm, particularly 31 to 35 nm, and especially 32 to 34 nm, and/or (ii) less than 16% by volume of particles having a volume diameter of less than 15 nm, preferably less than 12 nm, more preferably less than 9 nm, particularly less than 6 nm, and especially less than 4 nm below the median volume particle diameter, and/or (iii) less than 30% by volume of particles having a volume diameter of less than 8 nm, preferably less than 6 nm, more preferably less than 4 nm, particularly less than 3 nm, and especially less than 2 nm below the median volume particle diameter, and/or (iv) more than 84% by volume of particles having a volume diameter of less than 20 nm, preferably less than 15 nm, more preferably less than 10 nm, particularly less than 7 nm, and especially less than 5 nm above the median volume particle diameter, and/or (v) more than 70% by volume of particles having a volume diameter of less than 8 nm, preferably less than 6 nm, more preferably less than 4 nm, particularly less than 3 nm, and especially less than 2 nm above the median volume particle diameter (median volume particle diameter and particle size distribution measured using the same technique as for zinc oxide).

In addition, the transparent titanium dioxide particles (i) preferably have an extinction coefficient at 524 nm ($E_{524}$) of less than 2.0, more preferably in the range from 0.1 to 1.0, particularly 0.2 to 0.7, and especially 0.3 to 0.5 l/g/cm and/or (ii) preferably have an extinction coefficient at 450 nm ($E_{450}$) of less than 3.0, more preferably in the range from 0.1 to 2.0, particularly 0.5 to 1.5, and especially 0.7 to 1.0 l/g/cm, and/or (iii) suitably have an extinction coefficient at 360 nm ($E_{360}$) of greater than 3, preferably in the range from 4 to 10, more preferably 5 to 8, particularly 5.5 to 7.5, and especially 6 to 7 l/g/cm, and/or (iv) preferably have an extinction coefficient at 308 nm ($E_{308}$) of greater than 30, more preferably in the range from 35 to 65, particularly 40 to 60, and especially 45 to 55 l/g/cm, and/or (v) preferably have a maximum extinction coefficient E(max) in the range from 40 to 80, more preferably from 45 to 75, particularly 50 to 70, and especially 55 to 65 l/g/cm and/or (iv) preferably have a λ(max) in the range from 260 to 290, more preferably 265 to 285, particularly 268 to 280, and especially 270 to 275 nm (extinction values measured using the same basic technique as for zinc oxide).

A particularly preferred transparent titanium dioxide is available commercially as Solaveil Clarus (trade mark) from Uniqema.

A preferred embodiment is a dispersion comprising a mixture of particulate zinc oxide as defined herein and transparent particulate titanium dioxide as defined above, suitably at the following concentrations; (i) in the range from 1 to 30%, preferably 5 to 25%, more preferably 10 to 20%, particularly 12 to 18%, and especially 14 to 16% by weight of zinc oxide, and (ii) in the range from 10 to 50%, preferably 15 to 45%, more preferably 20 to 40%, particularly 25 to 35%, and especially 28 to 32% by weight of titanium dioxide. The ratio by weight of titanium dioxide to zinc oxide in the dispersion is preferably in the range from 0.5 to 5:1, more preferably 1 to 3:1, particularly 1.5 to 2.5:1, and especially 1.8 to 2.2:1.

A preferred sunscreen product comprises a mixture of (i) in the range from 0.1 to 15%, more preferably 0.5 to 10%, particularly 1 to 6%, and especially 2 to 4% by weight of particulate zinc oxide as defined herein, and (ii) in the range from 0.1 to 15%, more preferably 1 to 10%, particularly 3 to 8%, and especially 5 to 7% by weight of transparent particulate titanium dioxide as defined above.

Such a sunscreen product comprising a zinc oxide/titanium dioxide mixture can exhibit high UV protection, (i) suitably having a Sun Protection Factor (SPF) of greater than 10, preferably in the range from 13 to 45, more preferably 17 to 35, particularly 20 to 30, and especially 23 to 27; and/or reduced whiteness, (i) preferably having a change in whiteness ΔL of less than 4, more preferably less than 3, particularly less than 2.5, and especially less than 2.0.

The invention is illustrated by the following non-limiting examples.

In this specification the following test methods have been used to determine certain properties of the zinc oxide (and titanium dioxide) particles, and dispersions and sunscreen products containing the zinc oxide (and titanium dioxide) particles:

1) Particle Size Measurement of Primary Zinc Oxide Particles

A small amount of zinc oxide, typically 2 mg, was worked into approximately 2 drops of an oil, for one or two minutes on a flat surface using the tip of a steel spatula. The resultant suspension was diluted with solvent and a carbon-coated grid suitable for transmission electron microscopy was wetted with the suspension and dried on a hot-plate. Approximately 18 cm×21 cm photographs were produced at an appropriate, accurate magnification. Generally about 300-500 particles were displayed at about 2 diameters spacing. A minimum number of 300 primary particles were manually sized using a transparent size grid consisting of a row of circles of gradually increasing diameter, representing spherical particles. Each circle had ellipses of gradually increasing aspect ratio but equal volume beneath it. The outline of each particle was then fitted to the appropriate sphere or ellipse and logged against its equivalent spherical diameter. The mean particle diameter, and particle size distribution, of the particles were calculated from the above measurements. In addition, the aspect ratio of the particles was determined from the maximum and minimum dimensions of at least 100 particles. Alternatively, the measurements could be performed by computerised image analysis.

The basic method assumes log normal distribution standard deviations in the 1.2-1.6 range (wider crystal size distributions would require many more crystals to be counted for example of the order of 1000). The dispersion method described above has been found to be suitable for producing almost totally dispersed distributions of primary zinc oxide particles whilst introducing minimal crystal fracture. Any residual aggregates (or secondary particles) are sufficiently well defined that they, and any small debris, can be ignored, and effectively only primary particles included in the count.

2) Median Particle Volume Diameter and Particle Size Distribution of Zinc Oxide Particles in Dispersion A dispersion of zinc oxide particles was produced by mixing 9 g of polyhydroxystearic acid (weight average molecular weight approximately 1750) with 71 g of C12-C15 alkyl benzoate, and then adding 120 g of zinc oxide into the solution. The mixture was passed through a horizontal bead mill, operating at approximately 1500 r.p.m. and containing zirconia beads as grinding media for 15 minutes. The dispersion of zinc oxide particles was diluted to between 30 and 40 g/l by mixing with isopropyl myristate. The diluted sample was analysed on the Brookhaven BI-XDC particle sizer in centrifugation mode, and the median particle volume diameter and particle size distribution determined.

3) BET Specific Surface Area of Zinc Oxide Particles

The single point BET specific surface area was measured using a Micromeritics Flowsorb II 2300.

4) Change in Whiteness and Whiteness Index

A sunscreen formulation (as shown in Example 2) was coated on to the surface of a glossy black card and drawn down using a No 2 K bar to form a film of 12 µm wet thickness. The film was allowed to dry at room temperature for 10 minutes and the whiteness of the coating on the black surface ($L_F$) measured using a Minolta CR300 colourimeter. The change in whiteness $\Delta L$ was calculated by subtracting the whiteness of the substrate ($L_S$) from the whiteness of the coating ($L_F$) and expressing the value relative to the formulation containing 5% by weight of zinc oxide particles. The whiteness index is the percentage change in whiteness $\Delta L$ compared to a standard zinc oxide (=100% value) (Z-Cote (ex BASF)).

5) Sun Protection Factor

The Sun Protection Factor (SPF) of a sunscreen formulation was determined using the in vitro method of Diffey and Robson, J. Soc. Cosmet. Chem. Vol. 40, pp 127-133, 1989.

6) Extinction Coefficients 0.02 g of zinc oxide dispersion was made up to 100 ml with cyclohexane. The diluted sample was then placed in a spectrophotometer (Perkin-Elmer Lambda 2 UV/VIS Spectrophotometer) with a 1 cm path length and the absorbance, of UV and visible light measured. Extinction coefficients were calculated from the equation A=E.c.l, where A=absorbance, E=extinction coefficient in litres per gram per cm, c=concentration in grams per litre, and l=path length in cm.

EXAMPLES

Example 1

Particulate zinc oxide was produced by a modification of the French process. A zinc oxide dispersion was prepared by mixing 9 g of polyhydroxystearic acid with 71 g C12-C15 alkyl benzoate, and then adding 120 g of zinc oxide into the solution. The mixture was passed through a horizontal bead mill, operating at approximately 1500 r.p.m. and containing zirconia beads as grinding media for 15 minutes. The dispersion was diluted by adding 200 g of C12-C15 alkyl benzoate and subjected to a particle fractionation technique to remove larger particles from the dispersion.

The zinc oxide dispersion had the following extinction coefficients;

| $E_{524}$ | $E_{308}$ | $E_{360}$ | E (max) | λ (max) |
|---|---|---|---|---|
| 1.1 | 15.4 | 16.1 | 16.8 | 367 |

Example 2

A typical sunscreen formulation containing zinc oxide can be prepared as follows;

| | % by weight |
|---|---|
| Phase A: | |
| ARLACEL 165 (trade mark, ex Uniqema) | 6.0 |
| Stearyl alcohol | 0.75 |
| SPAN 60 (trade mark, ex Uniqema) | 0.75 |
| TWEEN 60 (trade mark, ex Uniqema) | 1.35 |
| White petroleum jelly | 4.0 |
| Silicone 200/350cs (ex Dow Corning) | 1.0 |
| Light mineral oil | 8.0 |
| Propylene glycol | 5.0 |
| Zinc Oxide dispersion produced in Example 1 | 15.0 |
| Phase B: | |
| Water; Pure | 48.9 |
| Keltrol RD (ex Kelco) | 0.2 |
| Glycerine BP | 5.0 |
| Aloe Vera Gel 10:1 (ex A & E Connock) | 0.7 |
| Phase C: | |
| Water; Pure | 2.5 |
| Phenonip (ex Clariant) | 0.6 |
| Germall 115 (ex ISP Sutton Laboratories) | 0.3 |

Procedure:

1. Heat phase A (except for zinc oxide) and phase B to 75° C.
2. Add zinc oxide to phase A; homogenise.
3. At 75° C., add A to B with high-shear mixing. Continue mixing for 2 minutes.
4. Begin cooling with moderate stirring. Add C at 45° C. Cool to 30° C. with stirring.

Example 3

A typical sunscreen formulation containing zinc oxide and transparent titanium dioxide can be prepared as follows;

|  | % by weight |
|---|---|
| Phase A: | |
| ARLACEL P135 (trade mark, ex Uniqema) | 2.0 |
| ARLAMOL HD (trade mark, ex Uniqema) | 5.8 |
| SOLAVEIL CT-100 (trade mark, ex Uniqema (titanium dioxide dispersion)) | 11.1 |
| Zinc oxide dispersion produced in Example 1 | 8.4 |
| Candelilla Wax (ex Eggar) | 1.0 |
| Phase B: | |
| Water; Pure | 66.5 |
| $MgSO_4 \cdot 7H_2O$ | 0.7 |
| PRICERINE 9091 (trade mark, ex Uniqema) | 4.0 |
| Phase C: | |
| Germaben II (ex ISP Sutton) | 0.5 |

Procedure:
1. Heat phases A and B separately to 75-80° C.
2. Slowly add B to A with intensive stirring.
3. Homogenise for approximately 2 minutes.
4. Cool to 45° C. with intensive stirring. Add C. Cool to room temperature with stirring.

The invention claimed is:

1. A dispersion comprising particles of zinc oxide in a dispersing medium wherein the zinc oxide particles in dispersion have (i) a median volume particle diameter in the range from 70 to 130 nm, (ii) more than 84% by volume of particles having a volume diameter of less than 57 nm above the median volume particle diameter, and wherein the zinc oxide particles have a maximum extinction coefficient E(max) in the range from 13 to 20 l/g/cm.

2. A dispersion according to claim 1 wherein the zinc oxide particles have a median volume particles diameter in the range from 80 to 120 nm, preferably 93 to 107 nm.

3. A dispersion according to claim 1, wherein more than 84% by volume of zinc oxide particles have a volume diameter of less than 54 nm above the median volume particles diameter.

4. A dispersion according to claim 1, wherein more than 70% by volume of particles have a volume diameter of less than 24 nm above the median volume particle diameter.

5. A dispersion according to claim 1, wherein the zinc oxide particles comprise primary particles having a mean particle size in the range from 35 to 65 nm.

6. A dispersion according to claim 1, wherein the zinc oxide particles have a BET specific surface area in the range from 15 to 35 $m^2/g$.

7. A dispersion according to claim 1, wherein the zinc oxide particles have a lead content of less than 10 ppm.

8. A dispersion according to claim 1, wherein the zinc oxide particles have an extinction coefficient at 524 nm ($E_{524}$) of less than 1.2 l/g/cm.

9. A dispersion according to claim 1, wherein the zinc oxide particles have an extinction coefficient at 450 nm ($E_{450}$) of less than 2.5 l/g/cm.

10. A dispersion according to claim 1, wherein the zinc oxide particles have an extinction coefficient at 360 nm ($E_{360}$) in the range from 12 to 20 l/g/cm.

11. A dispersion according to claim 1, wherein the zinc oxide particles have an extinction coefficient at 308 nm ($E_{308}$) in the range from 12 to 20 l/g/cm.

12. A dispersion according to claim 1, wherein the zinc oxide particles have a λ(max) in the range from 360 to 380 nm.

13. A dispersion according to claim 1, comprising at least 30% by weight of zinc oxide particles.

14. A particulate zinc oxide having a dispersion particle size of (i) median volume particle diameter in the range from 70 to 130 nm, (ii) more than 84% by volume of particles having a volume diameter of less than 57 nm above the median volume particle diameter, and wherein the zinc oxide particles have a maximum extinction coefficient E(max) in the range from 13 to 20 l/g/cm.

15. A particulate zinc oxide having an extinction coefficient at 524 nm ($E_{524}$) in the range from 0.1 to 1.0 l/g/cm, an extinction coefficient at 450 nm ($E_{450}$) in the range from 0.3 to 2 l/g/cm, an extinction coefficient at 360 nm ($E_{360}$) in the range from 12 to 20 l/g/cm, an extinction coefficient at 308 nm ($E_{308}$) in the range from 12 to 20 l/g/cm, a maximum extinction coefficient E(max) in the range from 14 to 20 l/g/cm, and a λ(max) in the range from 363 to 377 nm.

16. A sunscreen product comprising a zinc oxide or dispersion as defined in claim 1.

17. A sunscreen product according to claim 16 which is transparent when applied to the skin and has a change in whiteness ΔL in the range from 0.3 to 3.

18. A sunscreen product according to claim 16 having a whiteness index in the range from 5 to 80%.

19. A sunscreen product comprising (a) zinc oxide having a dispersion particle size of (i) median volume particle diameter in the range from 70 to 130 nm, (ii) more than 84% by volume of particles having a volume diameter of less than 57 nm above the median volume particle diameter, and wherein the zinc oxide particles have a maximum extinction coefficient E(max) in the range from 13 to 20 l/g/cm, and (b) titanium dioxide having a dispersion particle size of (i) median volume particle diameter in the range from 24 to 42 nm, (iii) more than 84% by volume of particles having a volume diameter of less than 20 nm above the median volume particle diameter.

20. A sunscreen product according to claim 19 wherein the titanium dioxide particles in dispersion (i) have less than 30% by volume of particles having a volume diameter of less than 8 nm below the median volume particle diameter, and/or (ii) have more than 70% by volume of particles having a volume diameter of less than 8 nm above the median volume particle diameter.

21. A sunscreen product according to claim 19, wherein the titanium dioxide particles (i) have an extinction coefficient at 524 nm ($E_{524}$) of less than 2.0 and/or (ii) have an extinction coefficient at 450 nm ($E_{450}$) of less than 3.0 and/or (iii) have an extinction coefficient at 360 nm ($E_{360}$) of greater than 3 and/or (iv) have an extinction coefficient at 308 nm ($E_{308}$) of greater than 30 and/or (v) have a maximum extinction coefficient E(max) in the range from 40 to 80 and/or (iv) have a λ(max) in the range from 260 to 290.

22. A sunscreen product according to claim 19, comprising in the range from 3 to 8% by weight of particulate titanium dioxide and in the range from 1 to 6% by weight of particulate zinc oxide.

* * * * *